(12) United States Patent
Jhaveri et al.

(10) Patent No.: US 11,581,079 B1
(45) Date of Patent: Feb. 14, 2023

(54) SYSTEM AND METHOD FOR VIRTUAL REVIEW OF A PHARMACEUTICAL PRODUCT FILLING PROCESS

(71) Applicant: WALGREEN CO., Deerfield, IL (US)

(72) Inventors: Nimesh S. Jhaveri, Kildeer, IL (US); Laura Jean Tebbe, Antioch, IL (US); Dejan Kozic, Wadsworth, IL (US); Fuli E, Mundelein, IL (US)

(73) Assignee: WALGREEN CO., Deerfield, IL (US)

( * ) Notice: Subject to any disclaimer, the term of this patent is extended or adjusted under 35 U.S.C. 154(b) by 265 days.

(21) Appl. No.: 16/657,464

(22) Filed: Oct. 18, 2019

Related U.S. Application Data

(63) Continuation of application No. 13/443,302, filed on Apr. 10, 2012, now abandoned.

(51) Int. Cl.
*G16H 20/13* (2018.01)
*G05B 15/02* (2006.01)

(52) U.S. Cl.
CPC ............. *G16H 20/13* (2018.01); *G05B 15/02* (2013.01)

(58) Field of Classification Search
CPC ................................ G16H 20/13; G05B 15/02
USPC ......................................................... 705/2–3
See application file for complete search history.

(56) References Cited

U.S. PATENT DOCUMENTS

| | | | |
|---|---|---|---|
| 4,869,394 A | 9/1989 | Hurst | |
| 5,597,995 A * | 1/1997 | Williams | G16H 20/13 235/375 |
| 5,907,493 A | 5/1999 | Boyer et al. | |
| 6,176,392 B1 * | 1/2001 | William | G07F 11/165 221/109 |
| 6,202,923 B1 | 3/2001 | Boyer et al. | |
| 6,535,637 B1 * | 3/2003 | Wootton | B65B 57/00 382/190 |
| 6,738,723 B2 * | 5/2004 | Hamilton | G06K 9/00 382/128 |
| 6,771,369 B2 | 8/2004 | Rzasa et al. | |
| 7,006,214 B2 * | 2/2006 | Rzasa | G01J 3/0291 356/300 |
| 7,058,584 B2 * | 6/2006 | Kosinski | G06Q 10/087 379/93.12 |

(Continued)

*Primary Examiner* — Michael Tomaszewski
(74) *Attorney, Agent, or Firm* — Marshall, Gerstein & Borun LLP; Randall G. Reuth

(57) ABSTRACT

Image based and network controlled, security systems and methods are disclosed herein for securely dispensing pharmaceutical products onsite at a physical location. A server receives scanned prescription image corresponding to a prescription of a user and determines a pharmaceutical product and a pharmaceutical product amount of the pharmaceutical product. The server receives, from a pharmaceutical product imaging device positioned within a physically secured pharmacy area, images of the pharmaceutical product, and then transmits, to a visualization user interface application executing on a network computer positioned outside the physically secured pharmacy area, a visual confirmation of the pharmaceutical product and the pharmaceutical product amount. The server receives, from the visualization user interface application, a verification of the visual confirmation, and updates, based on the verification, the user account with a ready state corresponding to the prescription, wherein the ready state indicates that the user may receive the pharmaceutical product.

20 Claims, 23 Drawing Sheets

(56) References Cited

U.S. PATENT DOCUMENTS

| | | | | |
|---|---|---|---|---|
| 7,668,618 | B2 * | 2/2010 | Szesko | G16H 70/40 700/214 |
| 7,702,525 | B2 * | 4/2010 | Kosinski | G06Q 40/08 705/2 |
| 7,720,694 | B2 | 5/2010 | Potuluri et al. | |
| 7,801,642 | B2 | 9/2010 | Ansari et al. | |
| 7,801,765 | B2 | 9/2010 | Denny | |
| 7,837,093 | B1 | 11/2010 | Leu et al. | |
| 7,848,934 | B2 * | 12/2010 | Kobylevsky | G06Q 40/08 705/2 |
| 7,860,724 | B2 * | 12/2010 | Chudy | G16H 20/10 705/2 |
| 7,912,582 | B1 | 3/2011 | Holtje et al. | |
| 7,941,325 | B2 | 5/2011 | Heald et al. | |
| 7,995,831 | B2 * | 8/2011 | Eller | G16H 70/40 382/142 |
| 8,046,242 | B1 | 10/2011 | daCosta et al. | |
| 8,060,248 | B1 | 11/2011 | Boyer et al. | |
| 8,060,380 | B2 * | 11/2011 | Sullivan | G06Q 40/08 705/2 |
| 8,072,635 | B2 | 12/2011 | Roberts et al. | |
| 8,136,332 | B2 * | 3/2012 | Rice | B65C 9/0015 53/445 |
| 8,145,501 | B1 | 3/2012 | Heald et al. | |
| 8,150,706 | B2 * | 4/2012 | Kobylevsky | G06Q 10/00 705/2 |
| 8,224,483 | B1 * | 7/2012 | Ansari | G06Q 10/087 700/240 |
| 8,239,217 | B2 | 8/2012 | Helmus et al. | |
| 8,244,587 | B2 * | 8/2012 | Denny | G06Q 40/08 705/22 |
| 8,295,582 | B2 * | 10/2012 | Eller | G16H 70/40 382/142 |
| 8,321,236 | B2 | 11/2012 | Goodall et al. | |
| 8,775,198 | B2 | 7/2014 | Wiener et al. | |
| 2004/0138921 | A1 * | 7/2004 | Broussard | G16H 20/13 705/2 |
| 2004/0172289 | A1 * | 9/2004 | Kozic | G16H 70/40 705/2 |
| 2006/0031097 | A1 | 2/2006 | Lipscher et al. | |
| 2006/0124656 | A1 * | 6/2006 | Popovich | G07F 17/0092 221/9 |
| 2007/0043469 | A1 | 2/2007 | Draper | |
| 2008/0056556 | A1 * | 3/2008 | Eller | G07F 17/0092 382/142 |
| 2009/0048863 | A1 * | 2/2009 | Kozlowski | G16H 80/00 705/2 |
| 2009/0048871 | A1 * | 2/2009 | Skomra | G16H 30/20 705/3 |
| 2009/0132083 | A1 | 5/2009 | Rice et al. | |
| 2010/0094653 | A1 * | 4/2010 | Tribble | G16H 10/60 235/375 |
| 2014/0156298 | A1 * | 6/2014 | Crawford | G16H 10/60 705/2 |

* cited by examiner

| Data Review | WAIT 21Min 3:02 PM | F1 | 1 | F4 | 10 | CMD 0 | TPR 8 | PFL 0 | MSC 7 |
|---|---|---|---|---|---|---|---|---|---|
| DUR Detail | PAT 0 Calls<br>PBR 0 Calls | FILL 52 | REV 6 | WCB 9 | DUR 15 | OOS 3 | STATS |

Test Patient | 09/06/1980 | 31 | M | (847) 222-3333 | 1234 Wilmot Dr., Deerfield, Il 600

1 Pat | 2 Pbr | 3 Plan | 4 PA | 5 Fax | 6 Store

Rx #: 205551  59166  NEW

Drug ID: ASPIRIN 325MG EC TABLETS         AC/HC: NSAIDS

Directions: TAKE AS DIRECTED

Last Fill Date: 09/06/2011

| Type | Severity | Rx # | Rx Date | Overridden |
|---|---|---|---|---|
| DRUG/ALLERGY-NSAIDS | MAJOR | | | N |
| | | | | |
| | | | | |
| | | | | |
| | | | | |

DUR Summary:
PRESCRIBED DRUG: ASPIRIN 325MG EC TABLETS
ADVERSE REACTION(S) REPORTED WITH PRIOR NSAIDS ADMINISTRATION:
SKIN RASHES/HIVES SHOCK/UNCONSCIOUSNESS ASTHMA/SHORTNESS OF BREATH NAUSEA/VOMITING/DIARREA ANEMIA/BLOOD DISORDERS Actions:
| Override All | Override | Create Exc |
| Drug Cmts | Consult Req | Close |

Tools:
| Drug Info Libr. | View Rx | Profile |
| Patient Cmts | Monograph |

Row 1 of 1

FIG. 8

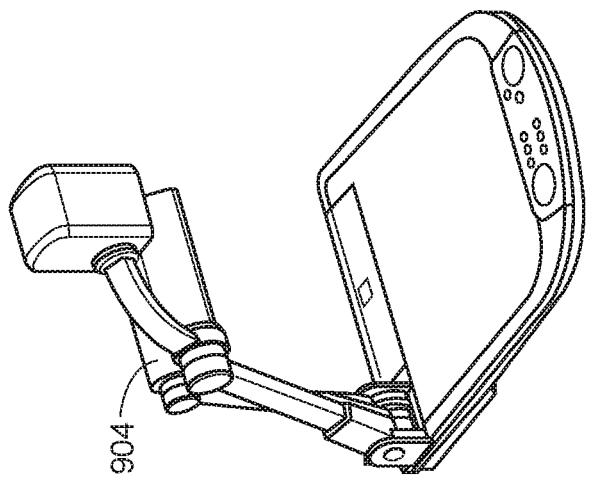
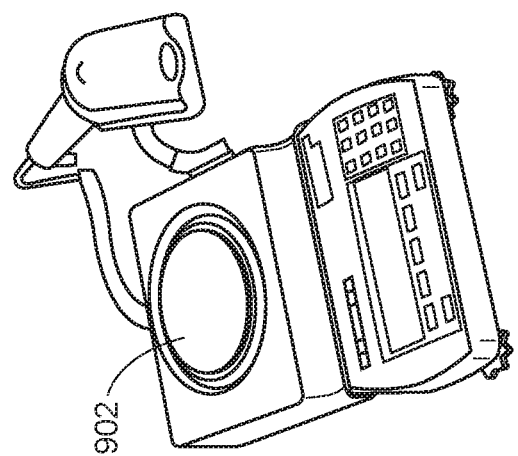
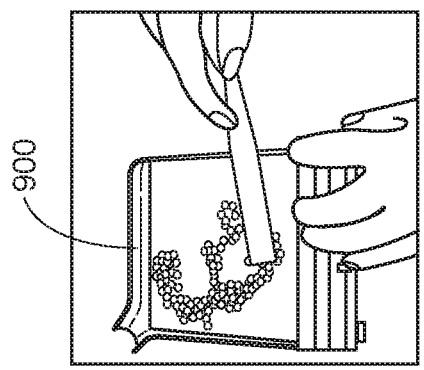
FIG. 9

SYSTEM AND METHOD FOR VIRTUAL REVIEW OF A PHARMACEUTICAL PRODUCT FILLING PROCESS

REFERENCE TO RELATED APPLICATIONS

This application is a continuation application that claims the benefit of U.S. application Ser. No. 13/443,302, filed Apr. 10, 2012. The entirety of the foregoing application is incorporated by reference herein.

FIELD OF THE DISCLOSURE

The present disclosure relates generally to pharmacy services, and more particularly to methods and apparatus to allow a pharmacist to remotely view and verify filled prescriptions.

BRIEF SUMMARY

In a typical pharmacy location, one or more pharmacists is typically assisted by one or more technicians or staff members working in the pharmacy. A customer with a prescription for a pharmaceutical product approaches a desk where a pharmacy staff member verifies the prescription and any insurance coverage information. A technician then typically fills the prescription for the pharmaceutical product specified on the prescription, including dispensing the prescribed quantity of the pharmaceutical product. The technician then takes the dispensed pharmaceutical product to a location where a pharmacist is located. The pharmacist then verifies the filled prescription to confirm that the requested pharmaceutical product and quantity of the pharmaceutical product were dispensed. The product is given to the customer only after the pharmacist verifies and approves the dispensed pharmaceutical product.

The present disclosure improves upon the above-described process by allowing a pharmacist who may not be at the same physical location as the technician to verify and approve the dispensed pharmaceutical product. This improvement is accomplished through the use of digitized images and networked computer systems.

Some of the many benefits of the present disclosure will be discussed below in the detailed description of the present disclosure.

BRIEF DESCRIPTION OF THE DRAWINGS

The present disclosure may be better understood by referring to the accompanying drawings, in which:

FIG. 6 illustrates a screenshot of an application for entering prescription data;

FIG. 7 illustrates a screenshot of an application for reviewing the prescription data of FIG. 6;

FIG. 8 illustrates a screenshot of an application for conducting a drug utilization review of the prescription data of FIG. 6;

FIG. 9 illustrates three devices that may be used in filling a prescription according an embodiment of the present disclosure;

FIG. 15 illustrates a screenshot of the application of FIG. 13 where an image of a filled prescription vial and a prescription leaflet have been captured;

FIG. 16 illustrates a screenshot of the application of FIG. 13 after the images of FIGS. 14 and 15 have been captured;

FIG. 18A illustrates unacceptable images of a prescription vial;

FIG. 21 illustrates a screenshot of the application of FIG. 20, where a pharmacist may accept or reject a prescription;

DETAILED DESCRIPTION

Although the following text sets forth a detailed description of numerous different embodiments, it should be understood that the legal scope of the invention is defined by the words of the claims set forth at the end of this patent. The detailed description is to be construed as exemplary only and does not describe every possible embodiment since describing every possible embodiment would be impractical, if not impossible. Numerous alternative embodiments could be implemented, using either current technology or technology developed after the filing date of this patent, which would still fall within the scope of the claims.

It should also be understood that, unless a term is expressly defined in this patent using the sentence "As used herein, the term '_____' is hereby defined to mean . . . " or a similar sentence, there is no intent to limit the meaning of that term, either expressly or by implication, beyond its plain or ordinary meaning, and such term should not be interpreted to be limited in scope based on any statement made in any section of this patent (other than the language of the claims). To the extent that any term recited in the claims at the end of this patent is referred to in this patent in a manner consistent with a single meaning, that is done for sake of clarity only so as to not confuse the reader, and it is not intended that such claim term be limited, by implication or otherwise, to that single meaning. Finally, unless a claim element is defined by reciting the word "means" and a function without the recital of any structure, it is not intended that the scope of any claim element be interpreted based on the application of 35 U.S.C. § 112, sixth paragraph.

Figure 1:
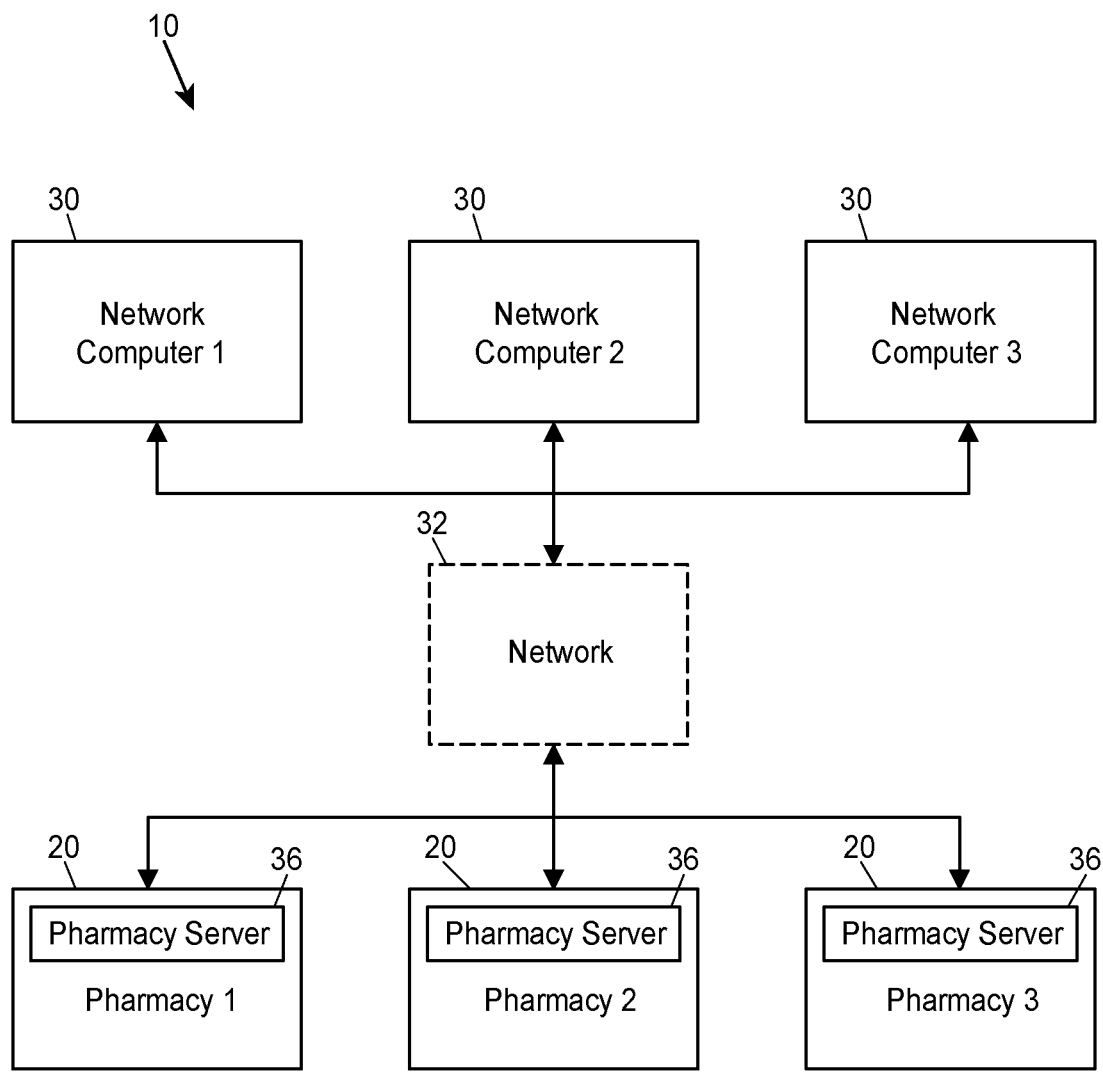
FIG. 1 illustrates block diagrams of computing systems that may operate in accordance with the described embodiments.

Turning to the drawings, FIG. 1 illustrates an embodiment of a data network 10 including a plurality of pharmacies 20 operatively coupled to a plurality of network computers 30 via a network 32. The plurality of pharmacies 20 may be located, by way of example rather than limitation, in separate geographic locations from each other, in different areas of the same city, or in different states. The network 32 may be provided using a wide variety of techniques well known to those skilled in the art for the transfer of electronic data. For example, the network 32 may comprise dedicated access lines, plain ordinary telephone lines, satellite links, Internet connections, or combinations of these. Where the network 32 comprises the Internet, data communications may take place over the network 32 via an Internet communications protocol.

The network computers 30 may include server computers of the type commonly employed in networking solutions. The network computer 30 may be used to accumulate, analyze, and download pharmacy data. For example, the network computers 30 may periodically receive data from each of the pharmacies 20 indicative of information pertaining to a prescription order, billing information, employee data, etc. The pharmacies 20 may include one or more facility servers 36 that may be used to store information for a plurality of customers/employees/accounts/etc. associated with each facility.

Although the data network 10 is shown to include three network computers 30 and three pharmacies 20, it should be understood that different numbers of computers and pharmacies may be used. For example, the data network 10 may include dozens of network computers 30 and dozens of pharmacies 20, all of which may be interconnected via the network 32. This configuration may provide several advantages, such as, for example, enabling near real time uploads and downloads of information as well as periodic uploads and downloads of information. This provides a primary backup of all the information generated in the process of updating and accumulating pharmacy data.

Figure 2:
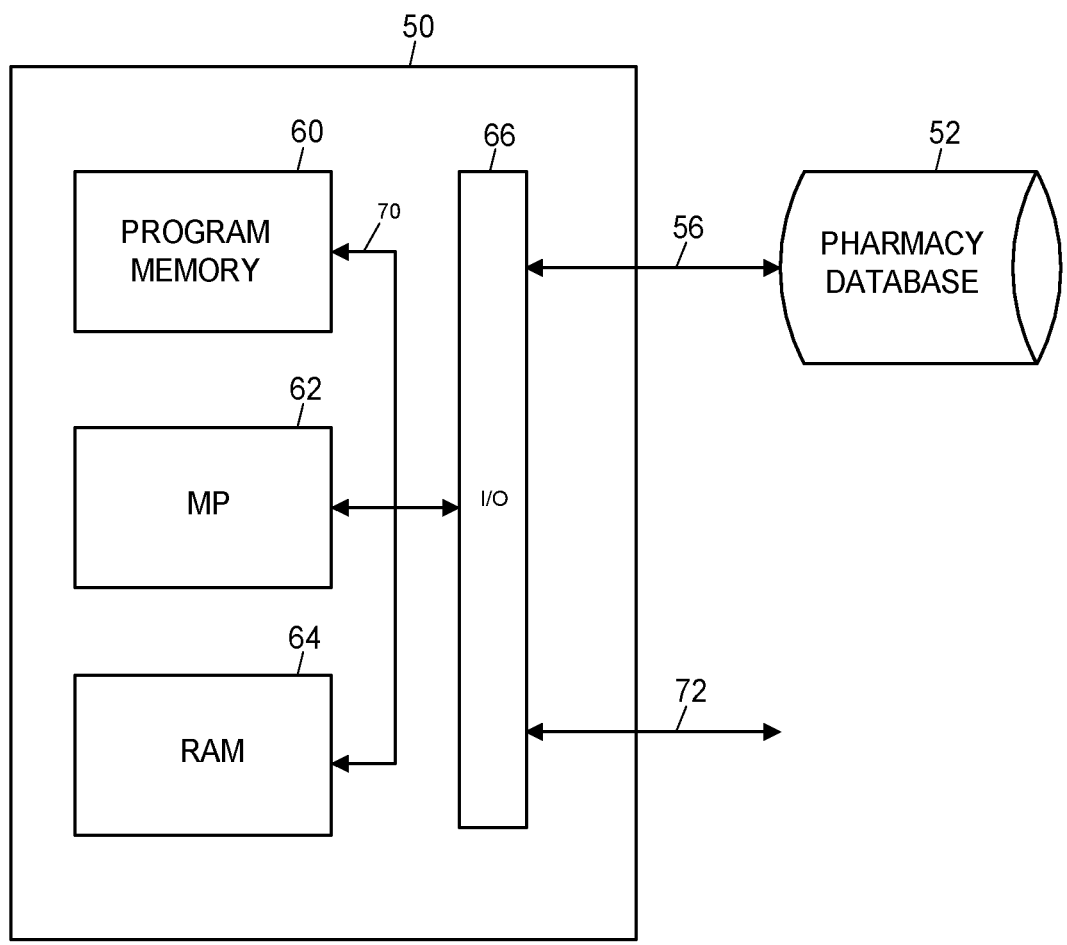
FIG. 2 illustrates further block diagrams of computing systems that may operate in accordance with the described embodiments.

FIG. 2 is a schematic diagram of one possible embodiment of a network computer 30 shown in FIG. 1. The network computer 30 may have a controller 50 that is operatively connected to a database 52 via a link 56. It should be noted that, while not shown, additional databases may be linked to the controller 50 in a known manner. The controller 50 may include a program memory 60, a microcontroller or a microprocessor (MP) 62, a random-access memory (RAM) 64, and an input/output (I/O) circuit 66, all of which may be interconnected via an address/data bus 70. It should be appreciated that although only one microprocessor 62 is shown, the controller 50 may include multiple microprocessors 62. Similarly, the memory of the controller 50 may include multiple RAMs 64 and multiple program memories 60. Although the I/O circuit 66 is shown as a single block, it should be appreciated that the I/O circuit 66 may include a number of different types of I/O circuits. The RAM(s) 64 and programs memories 60 may be implemented as semiconductor memories, magnetically readable memories, and/or optically readable memories, for example. The controller 50 may also be operatively connected to the network 32 via a link 72.

Figure 3:
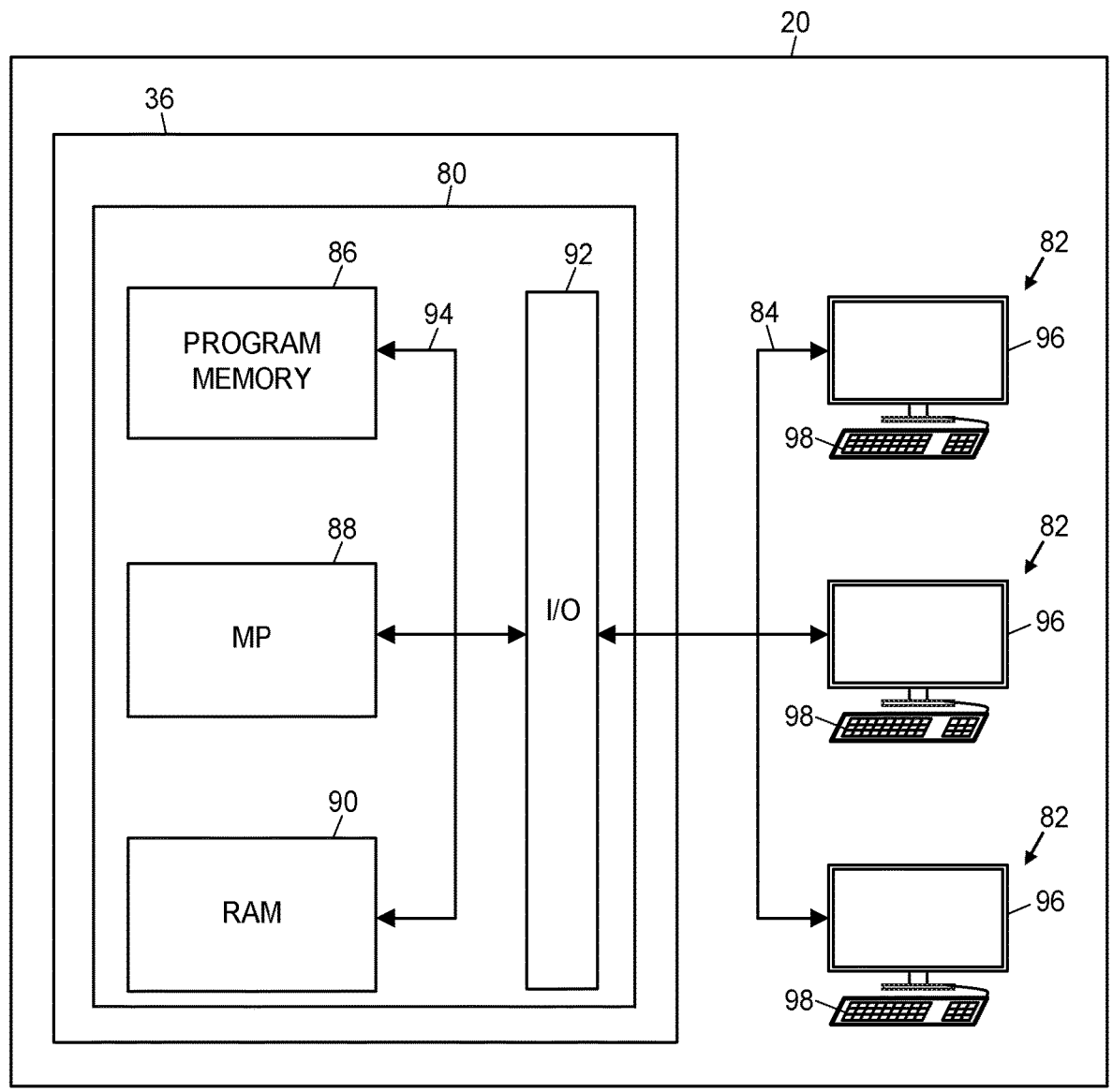
FIG. 3 illustrates still further block diagrams of computing systems that may operate in accordance with the described embodiments.

FIG. 3 is a schematic diagram of one possible embodiment of several components located in one or more of the pharmacies 20 from FIG. 1. Although the following description addresses the design of the pharmacies 20, it should be understood that the design of one or more of the pharmacies 20 may be different than the design of other pharmacies 20. Also, each pharmacy 20 may have various different structures and methods of operation. It should also be understood that the embodiment shown in FIG. 3 illustrates some of the components and data connections present in a pharmacy, however it does not illustrate all of the components and data connections present in a typical pharmacy. For exemplary purposes, one design of a pharmacy is described below, but it should be understood that numerous other designs may be used.

The pharmacies 20 may have a facility server 36, which includes a controller 80, wherein the facility server 36 is operatively connected to a plurality of client device terminals 82 via a network 84. The network 84 may be a wide area network (WAN), a local area network (LAN), or any other type of network readily known to those persons skilled in the art. The client device terminals 82 may also be operatively connected to the network computer 30 from FIG. 1 via the network 32.

Similar to the controller 50 from FIG. 2, the controller 80 may include a program memory 86, a microcontroller or a microprocessor (MP) 88, a random-access memory (RAM) 90, and an input/output (I/O) circuit 92, all of which may be interconnected via an address/data bus 94. As discussed with reference to the controller 50, it should be appreciated that although only one microprocessor 88 is shown, the controller 80 may include multiple microprocessors 88. Similarly, the memory of the controller 80 may include multiple RAMs 90 and multiple programs memories 86. Although the I/O circuit 92 is shown as a single block, the I/O circuit 92 may include a number of different types of I/O circuits. The RAM(s) 90 and programs memories 86 may also be implemented as semiconductor memories, magnetically readable memories, and/or optically readable memories, for example.

The client device terminals 82 may include a display and controller 96, a keyboard 98 as well as a variety of other input/output devices (not shown) such as a scanner, printer, mouse, touch screen, track pad, track ball, voice recognition system, etc. Each client device terminal 82 may be signed onto and occupied by a pharmacy employee to assist the employee in performing his or her duties. Pharmacy employees may sign onto a client terminal device 82 using any generally available technique, such as entering a user name and password. If a pharmacy employee is required to sign onto a client terminal device 82, this information may be passed via the link 84 to the facility server 36, so that the controller 80 will be able to identify which pharmacy employees are signed onto the system and which client device terminals 82 the employees are signed onto. This may be useful in monitoring the pharmacy employees' productivity.

Typically, facility servers 36 store a plurality of files, programs, and other data for use by the client device terminals 82 and the network computer 30. One facility server 36 may handle requests for data from a large number of client device terminals 82. Accordingly, each facility server 36 may typically comprise a high-end computer with a large storage capacity, one or more fast microprocessors, and one or more high-speed network connections. Conversely, relative to a typical facility server 36, each client device terminal 82 may typically include less storage capacity, a single microprocessor, and a single network connection.

Figure 4:
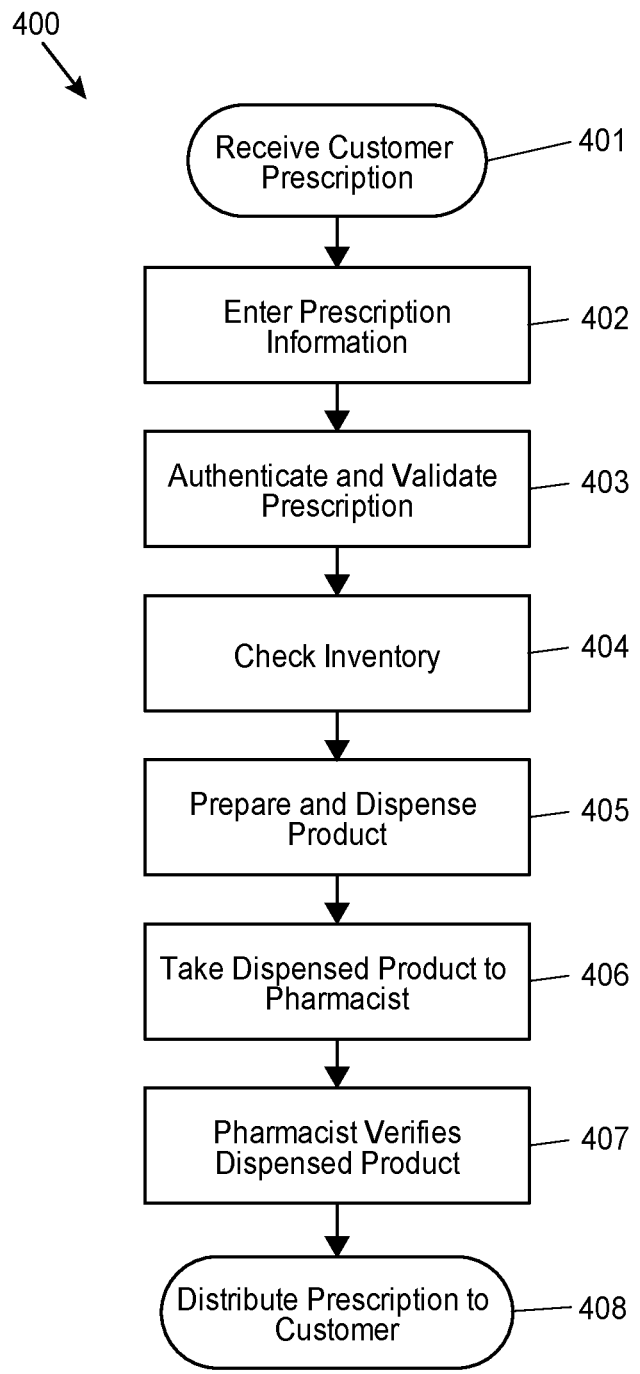
FIG. 4 illustrates a traditional pharmacy workflow.

FIG. 4 illustrates a workflow 400 for a traditional pharmacy store 20. Even though this pharmacy store 20 may be part of a large network of affiliated stores, the pharmacy store 20 processes each locally received prescription work order in-house independent of any other store. The parts of the workflow 400 may include a customer dropping off a prescription order to a pharmacy employee (e.g., pharmacist, technician or clerk) (block 401) after which the pharmacy employee begins processing the prescription by entering information into a computer (block 402). Thereafter, the pharmacy employee authenticates and validates the prescription (block 403) and does an inventory check to confirm availability of the pharmaceutical product (block 404). The pharmacy employee then physically prepares and dispenses the pharmaceutical product (block 405).

When the employee is not a pharmacist, the employee (e.g., technician) typically takes the dispensed pharmaceutical product to a different position within the pharmacy where a pharmacist is located (block 406). The pharmacist then verifies the filled prescription to confirm that the requested pharmaceutical product and quantity of the pharmaceutical product was dispensed (block 407). Once the pharmacist verifies and approves the dispensed pharmaceutical product, the product may be given to the customer (block 408).

The present disclosure improves upon the above-described process by allowing a pharmacist who is not in the same physical location as the pharmacy employee (e.g., a technician) to verify and approve the dispensed pharmaceutical product. In a pharmacy company comprising a network of affiliated stores, each pharmacy may be outfitted with apparatus to allow the pharmacy employee to capture digital images as the employee fills the prescription.

Figure 5:
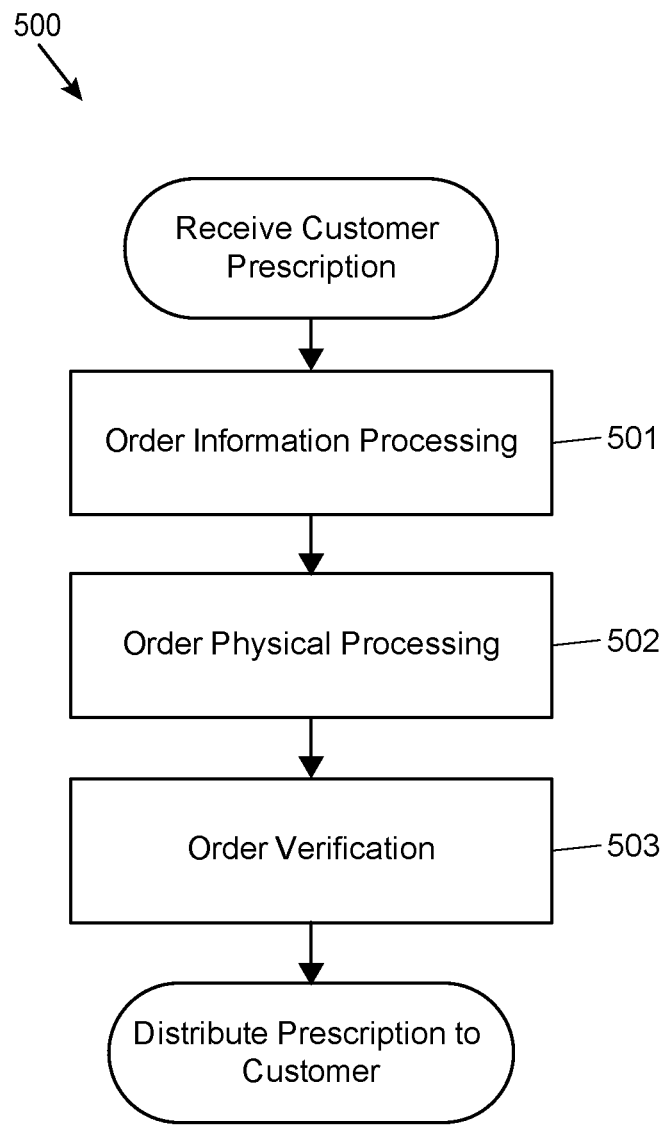
FIG. 5 illustrates the workflow of FIG. 4 condensed into similar tasks.

The workflow 400 illustrated in FIG. 4 may be grouped into similar steps, for example, as illustrated in FIG. 5. In FIG. 5, processing of a prescription drug order 500 may be separated into order information processing (block 501), order physical processing (block 502), and order verification (block 503). At least one of the activities illustrated in blocks 501-503 are performed outside the pharmacy or secured pharmacy area.

The order information processing (block 501) may include entering the original prescription order data into a system, for example at client device terminal 82, and any other actions that need to be performed to the order data before physically preparing the drug product. Because order information processing need not be performed at a particular location, the information processing portion of the order fulfillment process may be distributed to other organizational units. For example, a pharmacy employee may scan a prescription into a client device terminal 82 in a pharmacy 20 to create a prescription image. The client device terminal 82 may then cause the prescription image to be transmitted over the network 32 to a network computer 30, where an employee or contractor can manually enter the data from the scanned prescription image.

The order physical processing (block 502) may include the employee receiving approval to dispense a pharmaceutical product, including, for example, receiving a leaflet related to the prescription. The employee may then retrieve a bulk amount of the pharmaceutical product in order to start filling the prescription order. The pharmacy employee or a system or systems may then confirm that the bulk pharmaceutical product matches the product specified on the leaflet. This may be accomplished, for example, by scanning barcodes and the like located on the pharmaceutical product container and the leaflet, matching national drug code values on the pharmaceutical product container and the leaflet, or matching the pharmaceutical product names on the pharmaceutical product container and the leaflet.

The order verification (block 503) may include a pharmacist verifying a dispensed pharmaceutical product by confirming the dispensed amount of the product; confirming the size, shape, color of the dispensed product; confirming that a pharmaceutical product order leaflet matches information on a pharmaceutical product vial; and the like.

The redistribution of traditional pharmacy tasks may be especially useful in a corporate owned or franchise retail store network where a corporate entity may have the infrastructure to support this redistribution in a seamless manner. Such redistribution may allow the corporate entity to more efficiently use human resources, including, for example, specialized human resources, such a pharmacists and data entry clerks. For example, one pharmacist located at a network computer 30 may be able to service and verify orders from multiple pharmacies 20. This could be useful, for example, during nighttime hours where labor costs and labor utilization rates make staffing multiple pharmacies each with a pharmacist prohibitively expensive or, at the very least, cost inefficient. This could also be useful in allowing a pharmacist to verify prescriptions outside of a secured pharmacy area while the pharmacist is interacting with and counseling customers. In an embodiment of the present disclosure, a pharmacist may verify prescriptions using a mobile device such as a mobile phone or tablet computer, for example.

Figure 6:
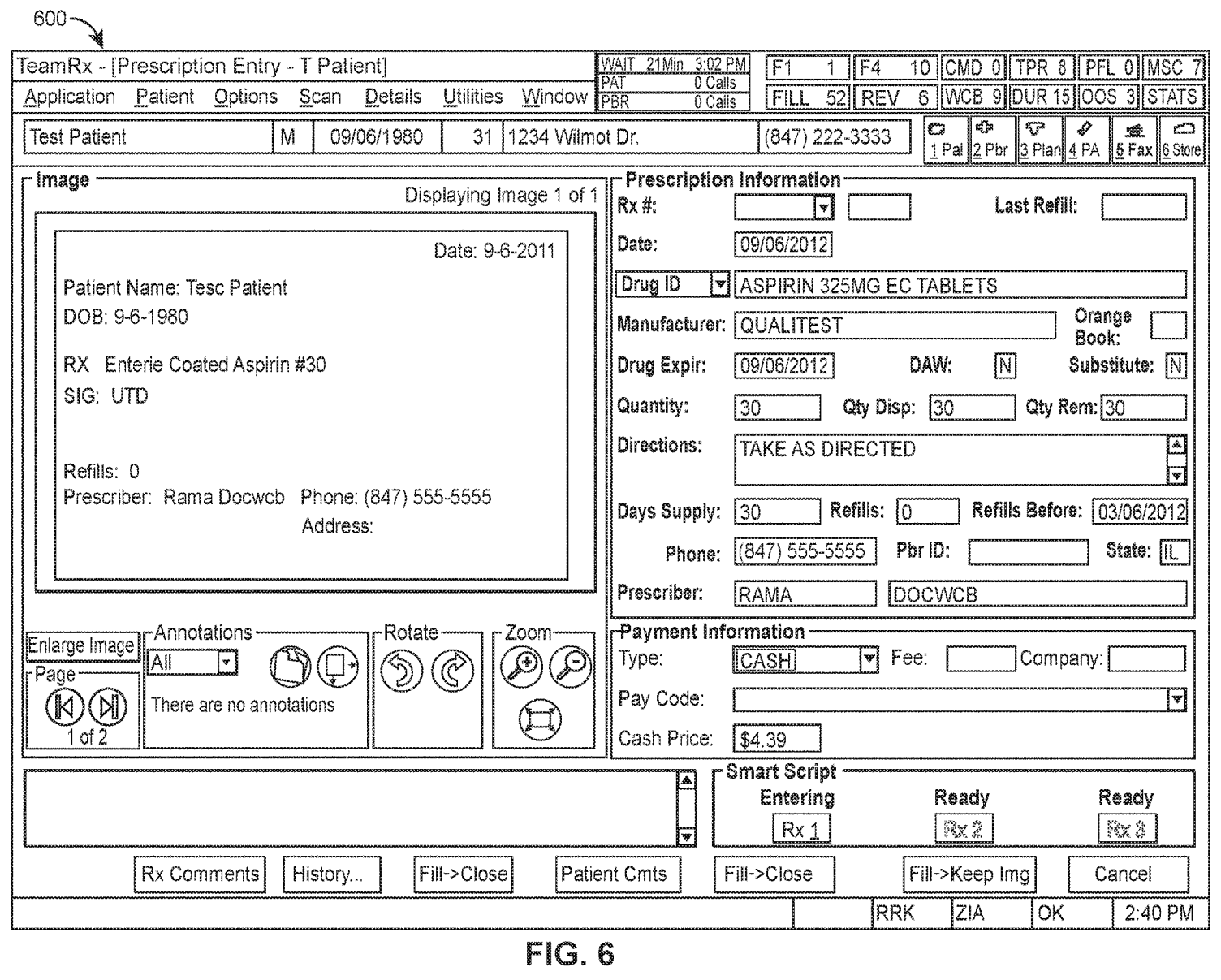

In a preferred embodiment of a process of the present disclosure, a pharmacy staff member first receives a customer's prescription and scans the prescription using, for example, an application 600 as illustrated in FIG. 6. The scanned prescription images are transmitted to a network computer 30 and stored in a non-transitory computer-readable medium for retrieval. In a preferred embodiment, an employee at a location outside of the pharmacy (e.g., a data processing center) retrieves the scanned prescription images and enters the prescription data into a software application that associates the prescription data with the scanned prescription images and the customer. However, in an alternate embodiment, the client device terminal 96 in the pharmacy 20, the network computer 30, or a network computer 30 located with the employee at a location outside the pharmacy 20 may comprise a software program to perform optical character recognition (OCR) of the prescription to extract the prescription data. Alternatively, the software program may read an indicium on the prescription, wherein the indicium digitally encodes at least a portion of the prescription data. The software program would then cause the prescription data to be stored and associated with the customer. The prescription could also be received electronically from a healthcare provider.

Figure 7:
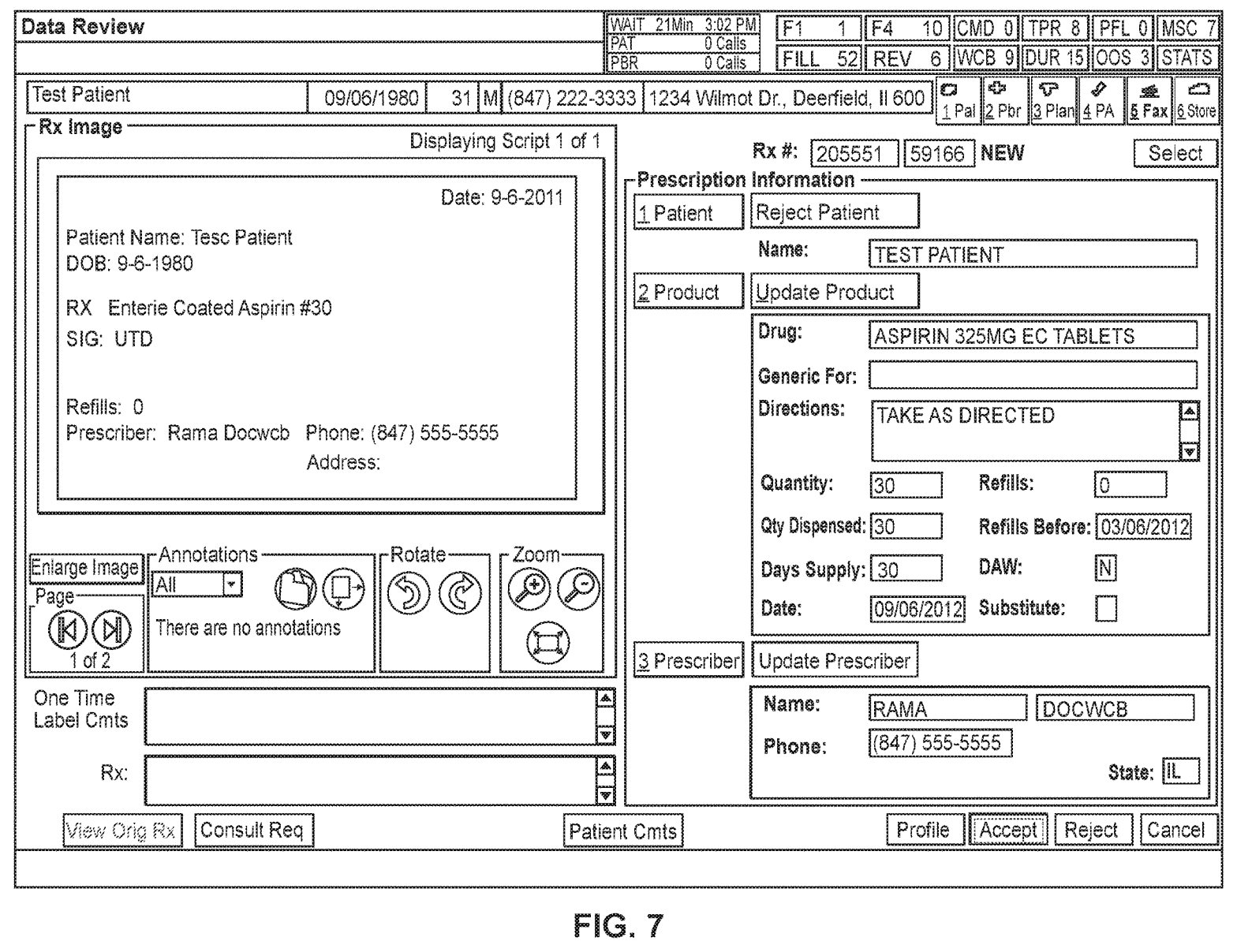

After the prescription data is stored and associated with the customer, a pharmacist then reviews the prescription data at a network computer 30 using a user interface as illustrated in FIG. 7 and conducts a drug utilization review (DUR) using the interface as illustrated in FIG. 8. At this stage, the pharmacist may approve or reject the prescription based on the prescription data or the DUR. If the pharmacist approves the prescription, an indication of the approval is transmitted to a network computer 30 and/or the client device terminal 82. Thereafter, the client device terminal 82 or a networked printer (not shown) is caused to output a leaflet with the prescription data. This leaflet may include, for example, a bar code associated with the pharmaceutical product to be dispensed.

The technician then retrieves the leaflet and the corresponding bulk pharmaceutical product. The technician then scans a barcode or other indicium (e.g., a national drug code or a product name) on the leaflet and a barcode (e.g., the manufacturer's barcode, a pharmacy-specific barcode) or other indicium (e.g., a national drug code or a product name) on the bulk pharmaceutical product to confirm the product to be dispensed. Upon confirmation of a match between the barcode or other indicium on the leaflet and the barcode or other indicium on the bulk pharmaceutical product, the prescription data may be displayed to assist the technician in dispensing the product. In an embodiment, an automated system may automatically retrieve and confirm the bulk pharmaceutical product without relying on the technician to scan a barcode or other indicium on the bulk pharmaceutical product. Thereafter, the technician counts the number of pharmaceutical units (e.g., pills or units of liquid) to be dispensed. The counting may be manual, automated using a scale, or automated using a pill counter.

Manual pill counting is a typical method of confirming the amount of pharmaceutical products dispensed. However, this method is prone to human errors and, therefore, is not the preferred method for use in the present disclosure due to the need for the pharmacist to remotely verify the dispensed product. On the other hand, manual dispensation may be required in certain situations, for example with products that are not easily counted using other methods and in situations where the other methods malfunction.

Weighing the dispensed product is another method of confirming the amount of pharmaceutical product dispensed. This method estimates the amount of dispensed product by dividing the weight of the dispensed product by the average weight of an individual unit of the product. This method can produce accurate product counts, but the method is susceptible to errors introduced by inconsistency of unit weights within and between batches of products. Turning to FIG. 9, a pharmacy employee may dispense the product using a dispensing instrument 900 and weigh the dispensed product using a scale 902. Thereafter, the employee may use the camera station 904 to capture digital images of the dispensed product, the prescription leaflet, the prescription label, and any other images or views that might be useful to a pharmacist remotely (outside a secured pharmacy area) verifying the dispensed product.

Figure 10:
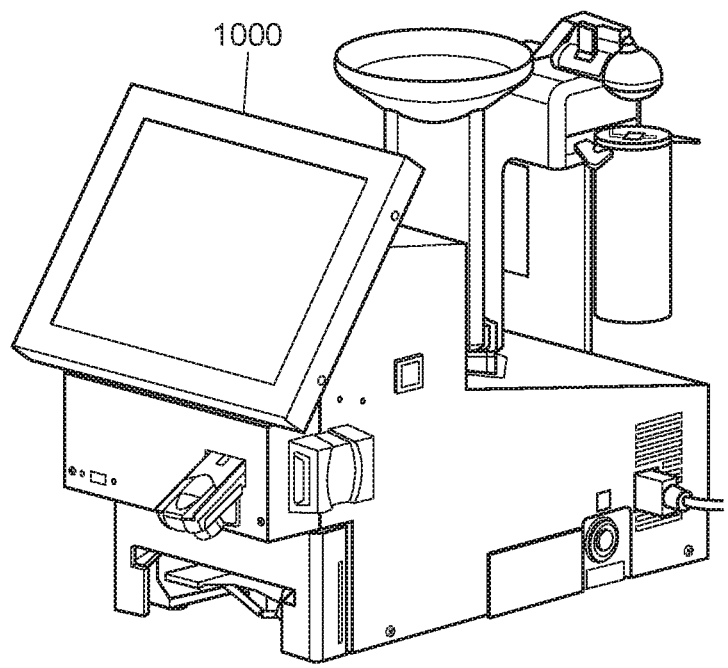
FIG. 10 illustrates an automated counting device that may be used in filling a prescription according to embodiments of the present disclosure.
Figure 11:
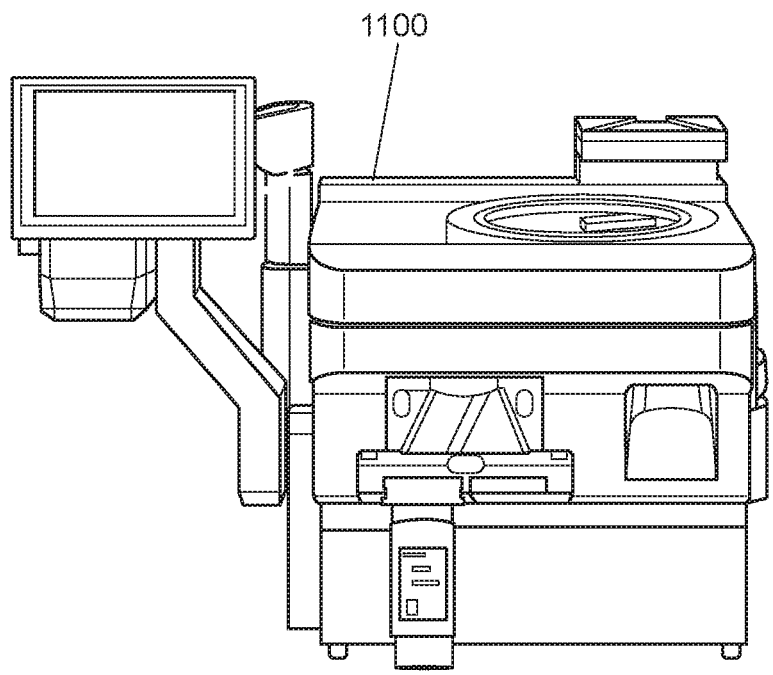
FIG. 11 illustrates a further automated counting device that may be used in filling a prescription according to embodiments of the present disclosure.
Figure 12:
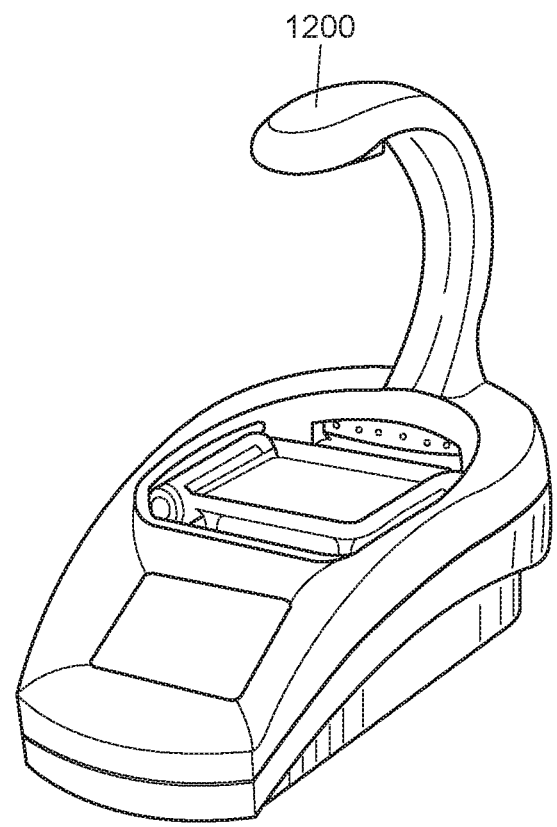
FIG. 12 illustrates a still further automated counting device that may be used in filling a prescription according to embodiments of the present disclosure.

Another method of confirming the amount of pharmaceutical product dispensed uses an automated counting and filling system. FIGS. 10-12 show examples of automated counting machines. FIG. 10 illustrates a counting device from Kirby Lester, LLC of Lake Forest, Ill.; FIG. 11 illustrates a counting device from Yuyama USA, Inc. of Elk Grove Village, Ill.; and FIG. 12 illustrates a counting device from Innovation Associates of Johnson City, N.Y. Each of these systems, while using different automated counting technologies, possess a high degree of accuracy in counting dispensed product.

Figure 13:
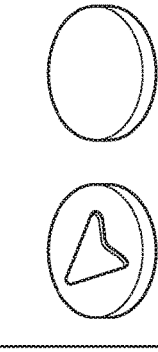
FIG. 13 illustrates a screenshot of an application to allow a technician to capture images while dispensing pharmaceutical products according to the prescription of FIG. 6.
Figure 14:
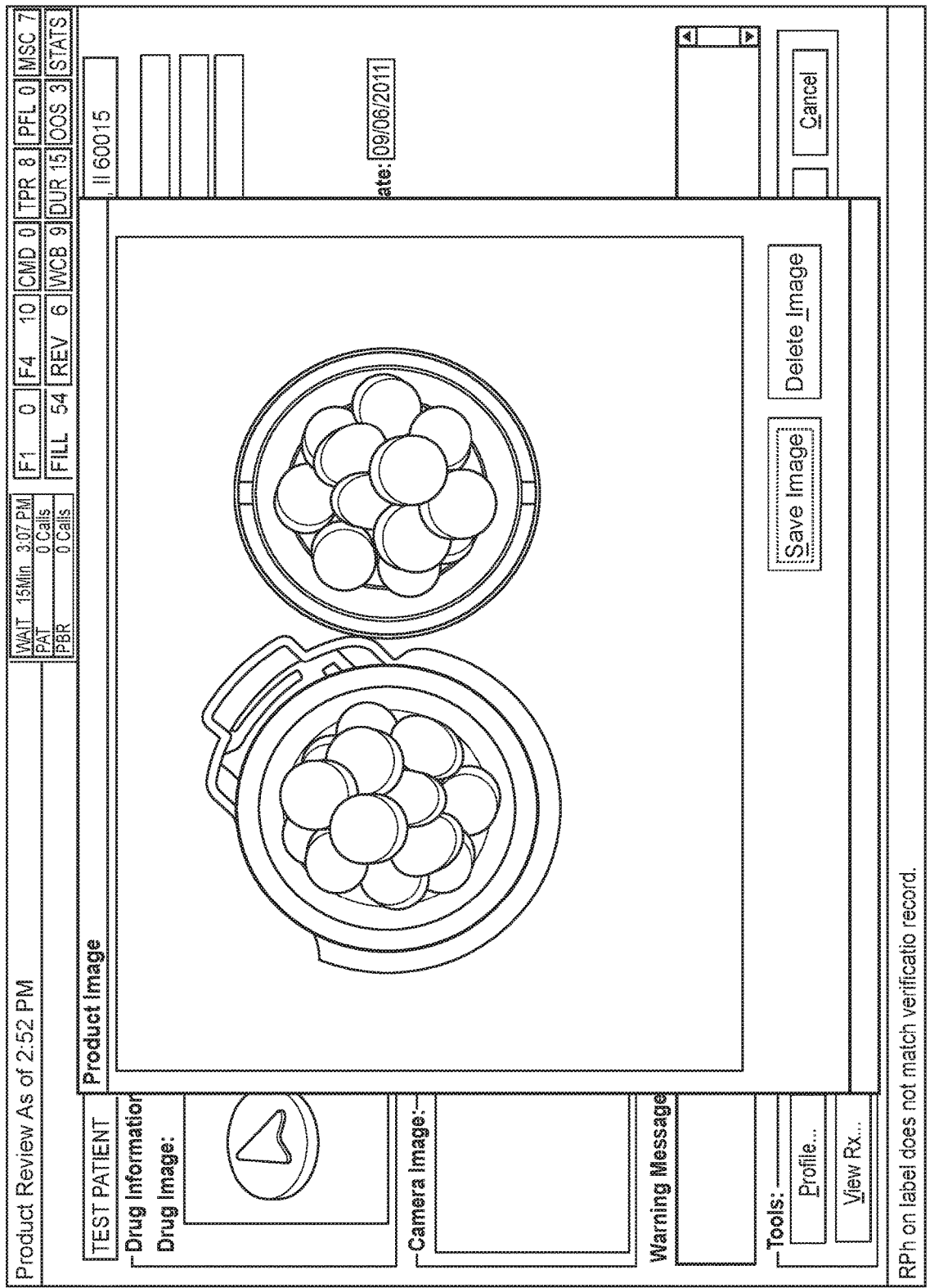
FIG. 14 illustrates a screenshot of the application of FIG. 13 where an image of a dispensed pharmaceutical product has been captured.
Figure 15:
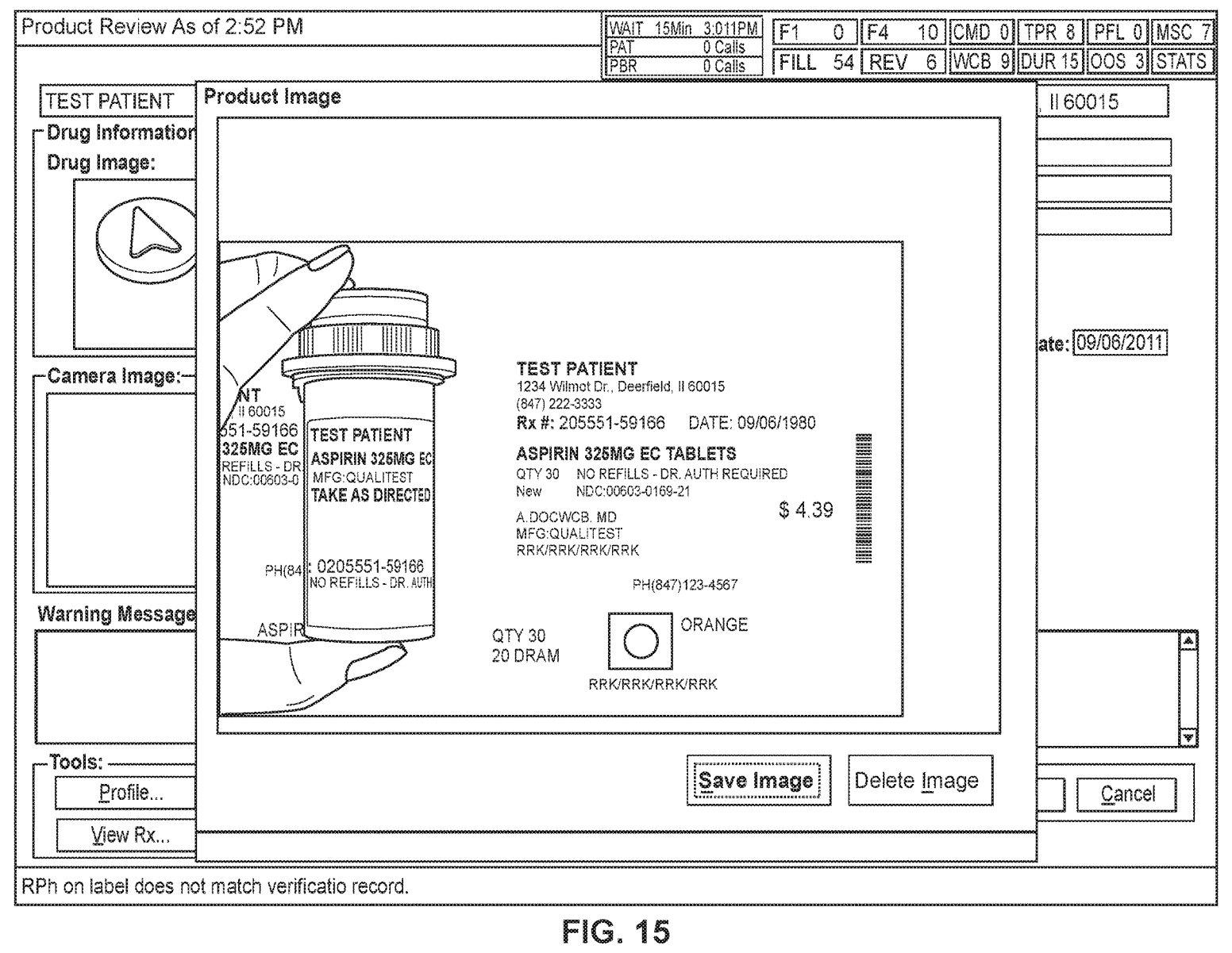
Figure 16:
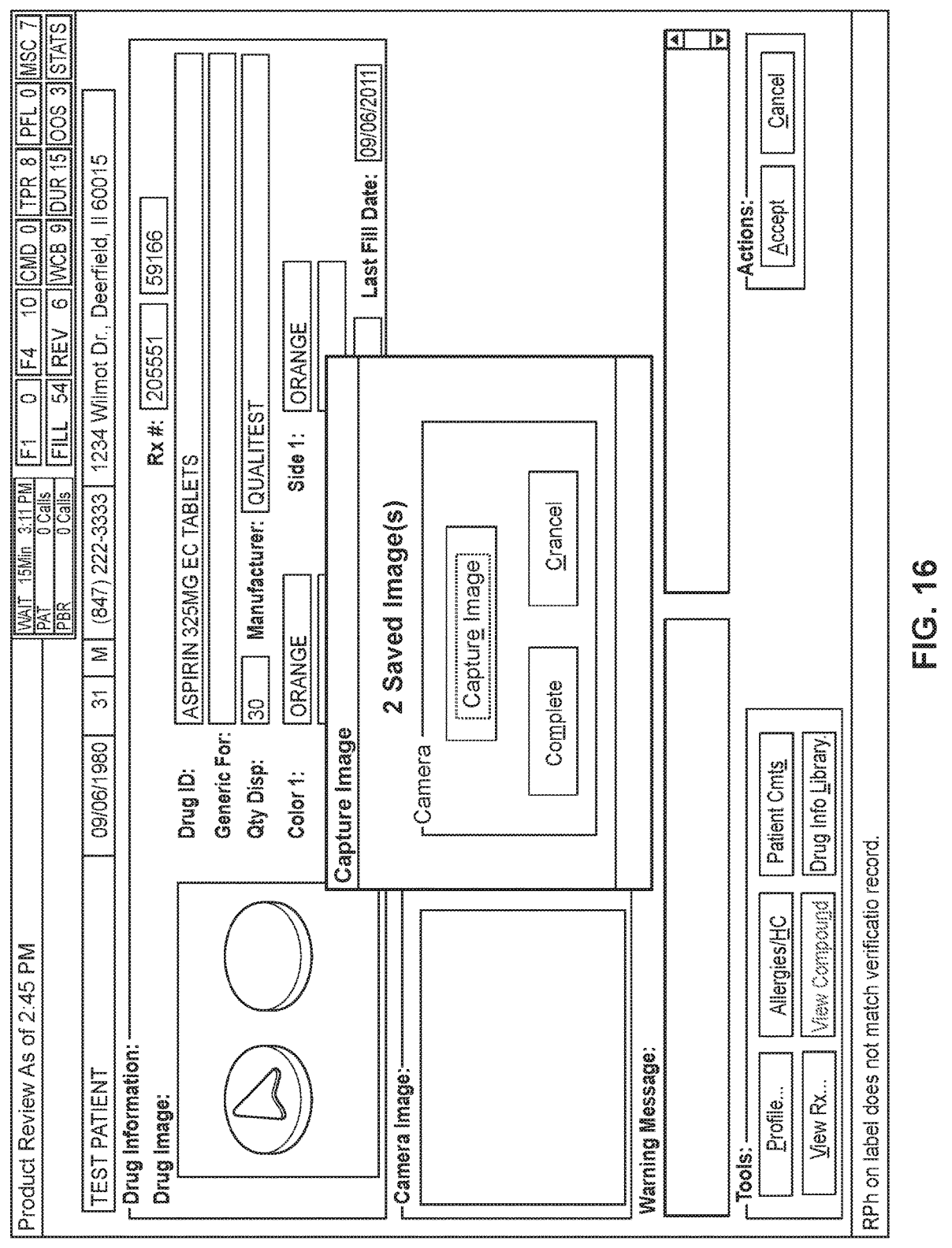

In each of the embodiments above, once the technician accepts the product count, a product review window appears on a user interface, for example the user interface illustrated in FIG. 13, and a camera in proximity to the scale is activated. A printer also outputs a prescription label for the vial in which the product will be dispensed. The technician then applies the prescription label to the vial. Thereafter, the technician places the dispensed product into the vial. In an embodiment, an indicium on the prescription label of the vial may be scanned and matched against an indicium on the leaflet and/or an indicium on the bulk pharmaceutical product container before the vial is filled with the pharmaceutical product. Thereafter, the technician takes pictures of the product in the vial, the labeled vial, and the leaflet, as illustrated in FIGS. 14 and 15. The technician then reviews and accepts the images using, for example, the user interface illustrated in FIG. 16. The client device terminal 82 then causes the images to be transmitted to a remote database or a network computer 30, where the network computer 30 is a server or a terminal associated with a pharmacist. Alternatively, the client device terminal 82 may cause the images to be stored in a local database. This allows the pharmacist to review images of the dispensed pharmaceutical product.

In some embodiments of the present disclosure, the counting and imaging may be automated and integrated into a single system. For instance, the systems of FIGS. 10-12 may include cameras and software operable to cause the systems and cameras to capture images of the pharmaceutical product as the order is being filled. The software also may be operable to automatically cause the images to be transmitted to a network computer 30 for review by a pharmacist. In some embodiments, the systems of may replace the client device terminal 82. In some embodiments, the systems of FIGS. 10-12 may also be configured to print a prescription order leaflet. In other embodiments, the systems of FIGS. 10-12 may be configured scan an indicium on a prescription order leaflet and an indicium on a bulk pharmaceutical product container and compare the indicia to confirm a match between the prescription and the pharmaceutical product. In some embodiments of the systems of FIGS. 10-12, a prescription label may be automatically applied to a prescription vial before, during, or after a pharmaceutical product is dispensed into the vial.

Once the pharmacist has reviewed and approved the dispensed product based on the images, the approval causes the prescription status at the pharmacy to change to a state indicating that the prescription may be distributed to the customer. This may include, for example, the prescription status changing to a "ready" state on a waitlist queue monitor visible to the pharmacy employees and/or the customer. Thereafter, the customer picks up his or her filled prescription from the drop off/pickup window of the pharmacy.

It will be understood by those of ordinary skill in the art that parts of this process may occur in the same physical location or the parts of the process may be distributed across a combination of different physical locations. Furthermore, parts of the process may occur at different positions within the same physical location. For example, the pharmacist may be located within the same pharmacy as the technician who fills the prescription, but the pharmacist may be positioned away from the technician, such as, for example, out of the secured pharmacy area.

The above-described process is based on the pharmacist being located at a position or location different from the technician filling the prescription. Therefore, it is important that the technician takes care to always send the pharmacist clear images of the customer leaflet, the labeled vial or labeled product, and the units in the vial. This preferably includes ensuring that any "pharmacy use only" portion of the leaflet is clear so that the pharmacist may verify the drug, dose, and the customer's information. The technician should preferably label the vial or product before capturing the images so that the pharmacist is assured that the correct label has been placed on the vial being filled. Furthermore, the technician should preferably capture images of the filled prescription from multiple viewpoints to show features such as shape, dimension, and markings as well as using the camera to zoom in where necessary to allow the pharmacist to verify the product is correct.

Figure 17A:
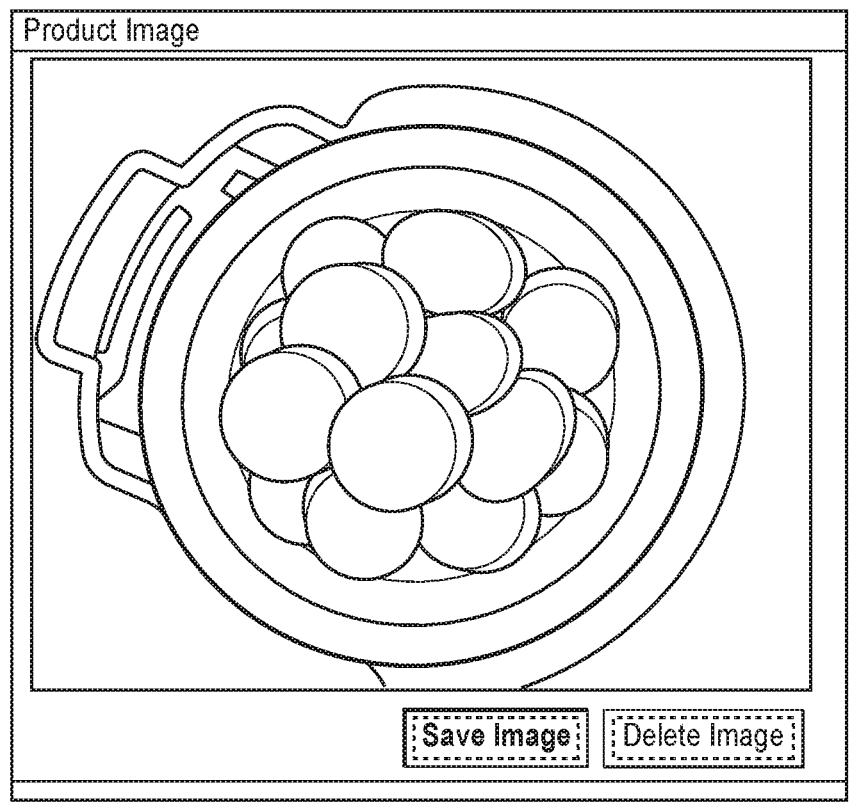
FIG. 17A illustrates acceptable images of pharmaceutical pills.
Figure 17B:
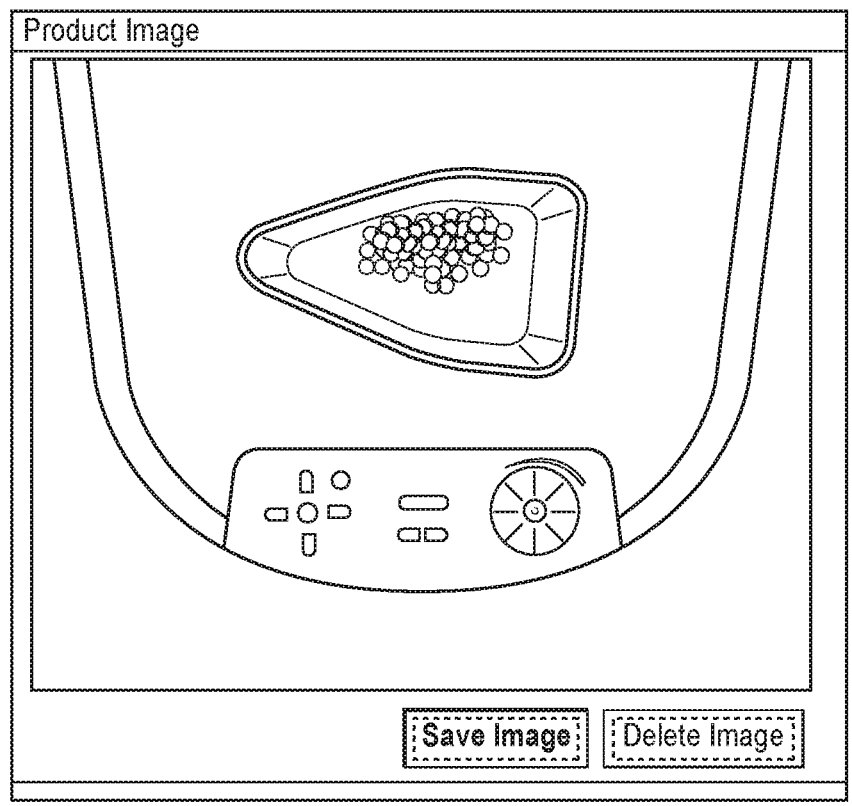
FIG. 17B illustrates unacceptable images of pharmaceutical pills.

FIGS. 17A and 17B respectively illustrate an acceptable and an unacceptable image of dispensed pills. In FIG. 17A, the image is large and clear, and there are multiple views of the dispensed units, giving the pharmacist an indication of the shape, dimension, and color of the dispensed units. Furthermore, the large image allows the pharmacist to view markings on the dispensed units, if there are any. In contrast, FIG. 17A illustrates an unacceptable image. In FIG. 17B, the dispensed pills are too far from the camera. This image does not allow the pharmacist to see multiple views of the units or any markings on the units, unlike with FIG. 17A.

Figure 18A:
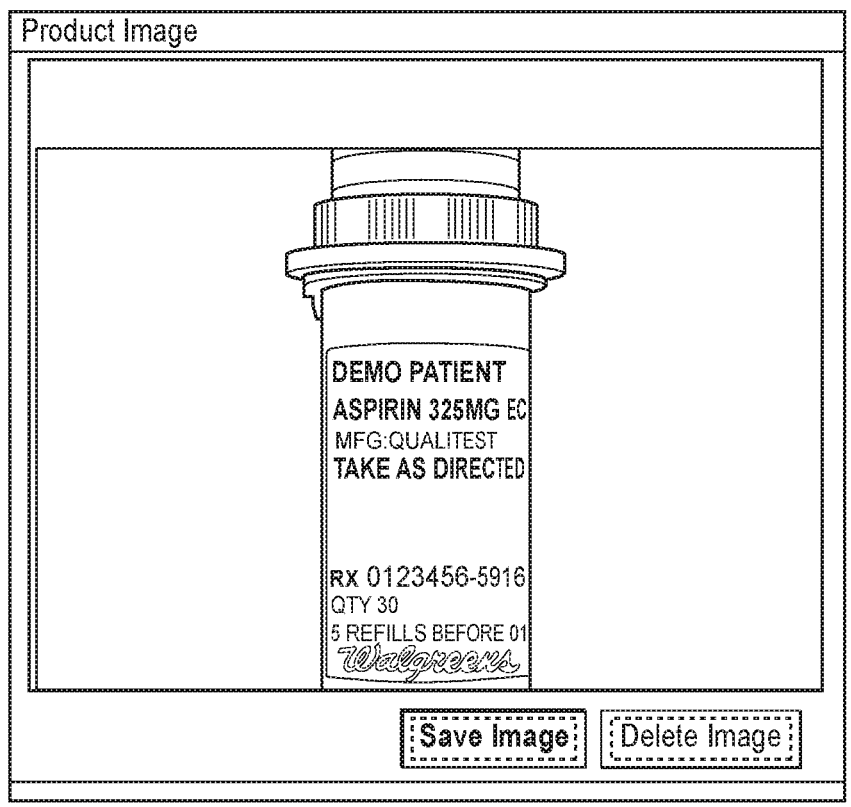
FIG. 18A illustrates acceptable images of a prescription vial.
Figure 18B:
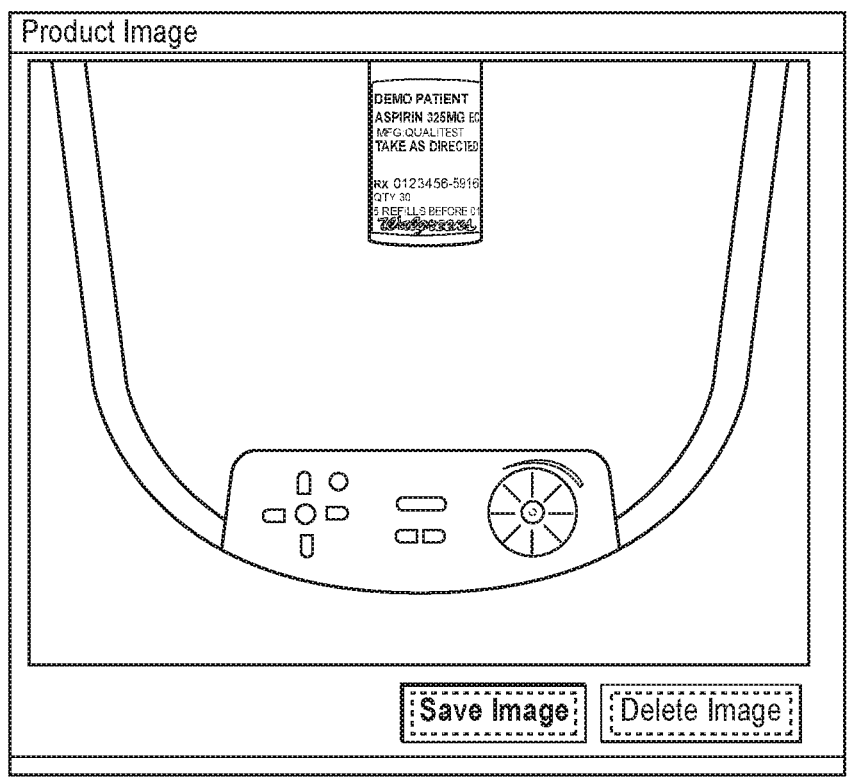

FIGS. 18A and 18B respectively illustrate an acceptable and an unacceptable image of a labeled prescription vial. In FIG. 18A, the image is large and clear, and the drug name, the customer name, and the prescription number are all clear and visible. In contrast, FIG. 18B illustrates an unacceptable image of the prescription vial. In FIG. 18B, the labeled prescription vial is too far from the camera, and the drug name, customer name, and prescription number are not visible.

Figure 19A:
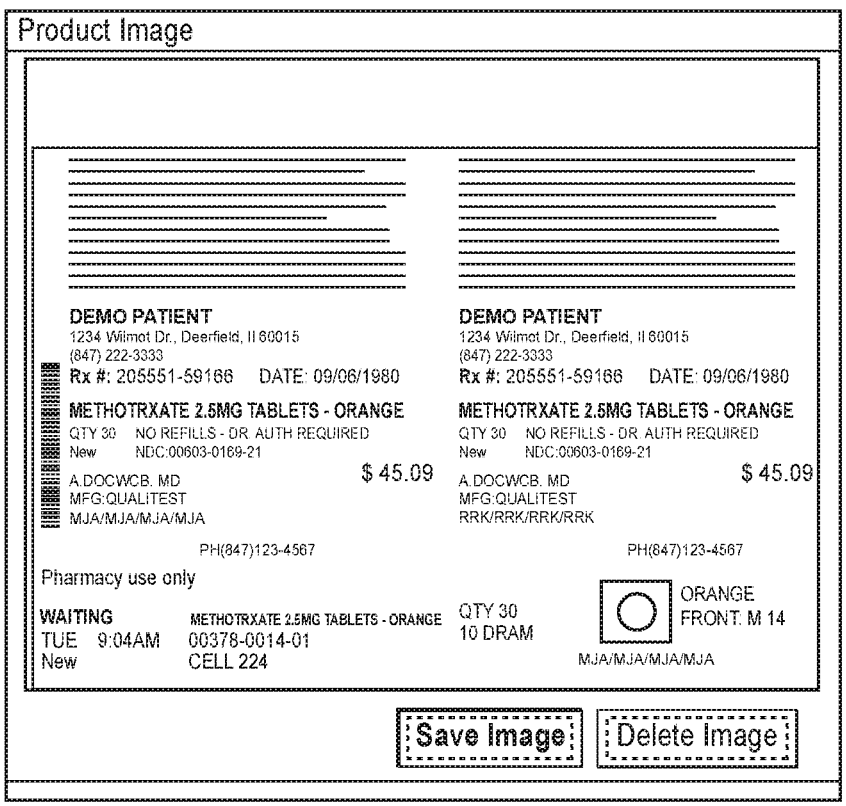
FIG. 19A illustrates acceptable images of a prescription leaflet.
Figure 19B:
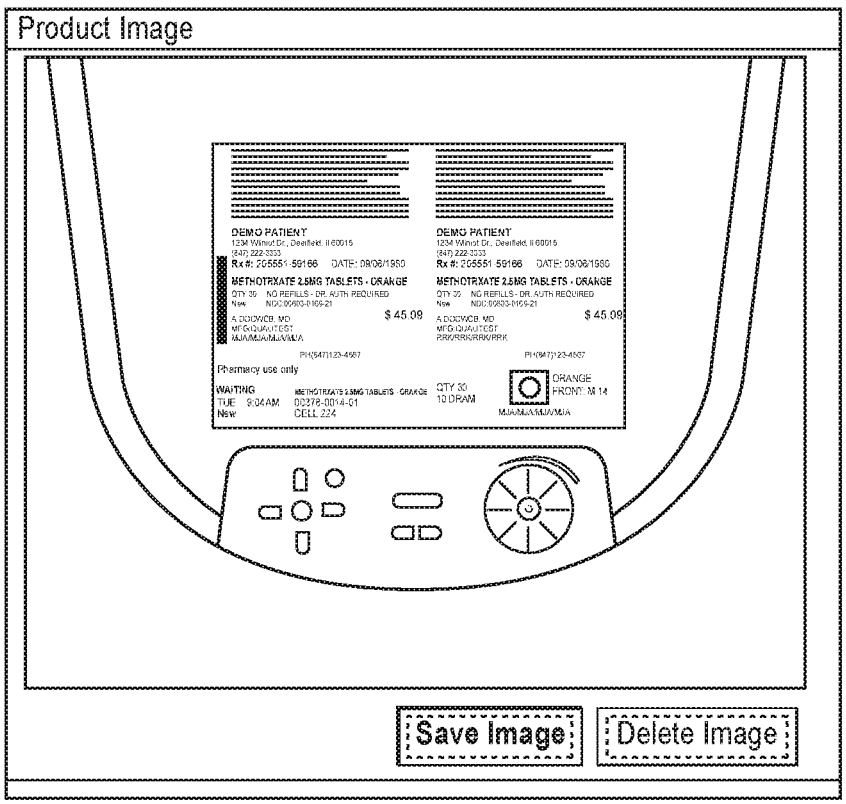
FIG. 19B illustrates unacceptable images of a prescription leaflet.

FIGS. 19A and 19B respectively illustrate an acceptable and an unacceptable image of a customer leaflet. In FIG. 19A, the image is large and clear, and the "pharmacy use only" section, the drug name and dose, the customer name, and the prescription number are all clear and visible. In contrast, FIG. 19B illustrates an unacceptable image of the customer leaflet. In FIG. 19B, the customer leaflet is too far from the camera, and the "pharmacy use only" section, the drug name and dose, the customer name, and the prescription number are not visible.

Figure 20:
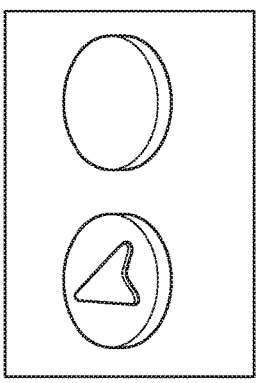
FIG. 20 illustrates a screenshot of an application for reviewing images of a filled prescription.
Figure 21:
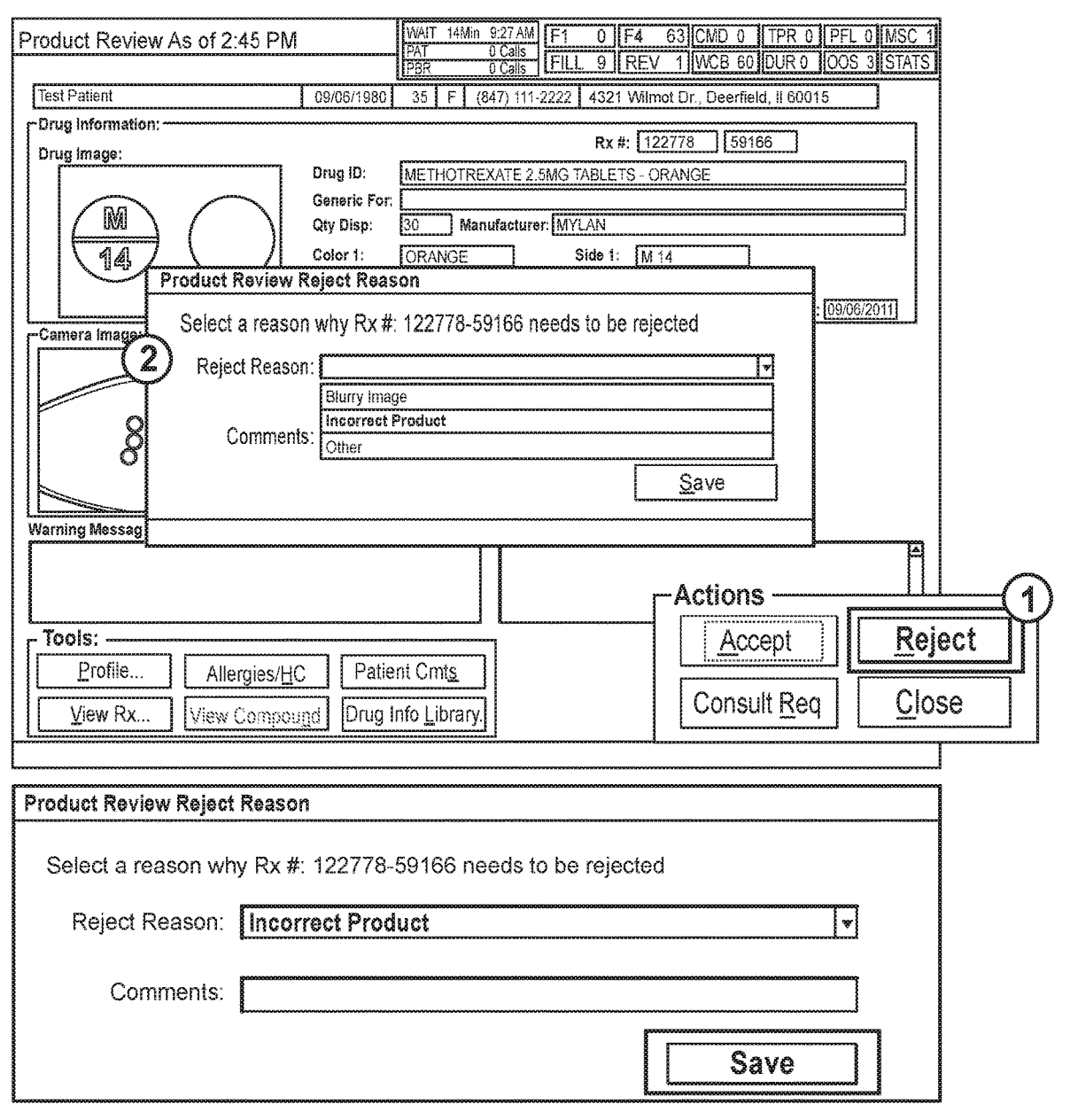

The pharmacist remotely viewing the images using the user interface illustrated in FIG. 20, for example, may reject a prescription if the images are unacceptable. In this case, the pharmacist may select the reject button 2002 of the user interface illustrated in FIG. 20. A popup window illustrated in FIG. 21b may appear prompting the pharmacist to enter a reason for rejecting the prescription. These reasons may include, for example, that one or more of the images are blurry or unreadable, that the incorrect product was dispensed, the images show a wrong leaflet, or any other reason why the pharmacist deems it necessary to reject the prescription.

Figure 22:
FIG. 22 illustrates a prescription pickup queue.

The pharmacist's rejection of the prescription causes an indication to be transmitted to the technician, for example to the client device terminal 82 or to a prescription pickup monitor as illustrated in FIG. 22. The technician will then be required to refill the prescription. In a preferred embodiment of the present disclosure, the technician would be required to retrieve and scan the rejected prescription before being able to refill the prescription. This requirement may serve as a quality control measure to help ensure that the rejected prescription is not sold to the customer. The rejected prescription may then be returned to the pharmaceutical product stock. Thereafter, a new customer leaflet is printed and the process and methods of the present disclosure are restarted.

If, on the other hand, the pharmacist deems the prescription to be acceptable, the pharmacist may accept the prescription by selecting the accept button 2004 of the user interface illustrated in FIG. 20, for example. This causes an indication to be sent to the client device terminal 82 and/or a prescription pickup monitor indicating that the prescription may be given to the customer. This indication may also include causing the prescription's status to change to a "ready" state.

Those skilled in the art would understand that while the above-described embodiments may describe pharmaceutical pills, variations in the above-described embodiments may be needed when the unit to be dispensed is a liquid or a multiple unit of use (e.g., multiple packs of birth-control pills).

Figure 23:
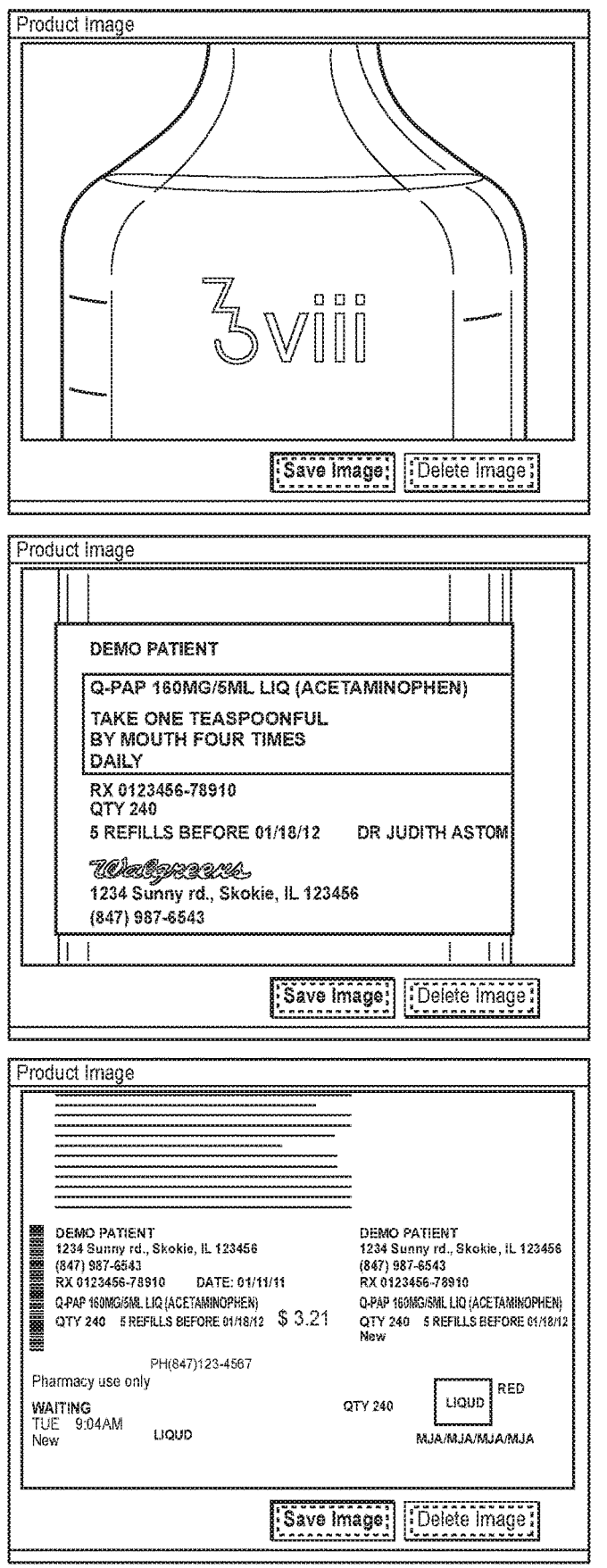
FIG. 23 illustrates images of a filled prescription, where the pharmaceutical product is a liquid.

In an embodiment involving dispensing a liquid product, the technician may be required to provide the pharmacist visual confirmation of the drug and amount of the liquid drug dispensed, for example as illustrated in FIG. 23. To accomplish this, the technician may use the camera to capture an image of the stock bottle from which the liquid product will be dispensed and the bottle into which the product was dispensed. This may involve the technician repositioning the camera to a position different from that used when dispensing non-liquid product.

Figure 24:
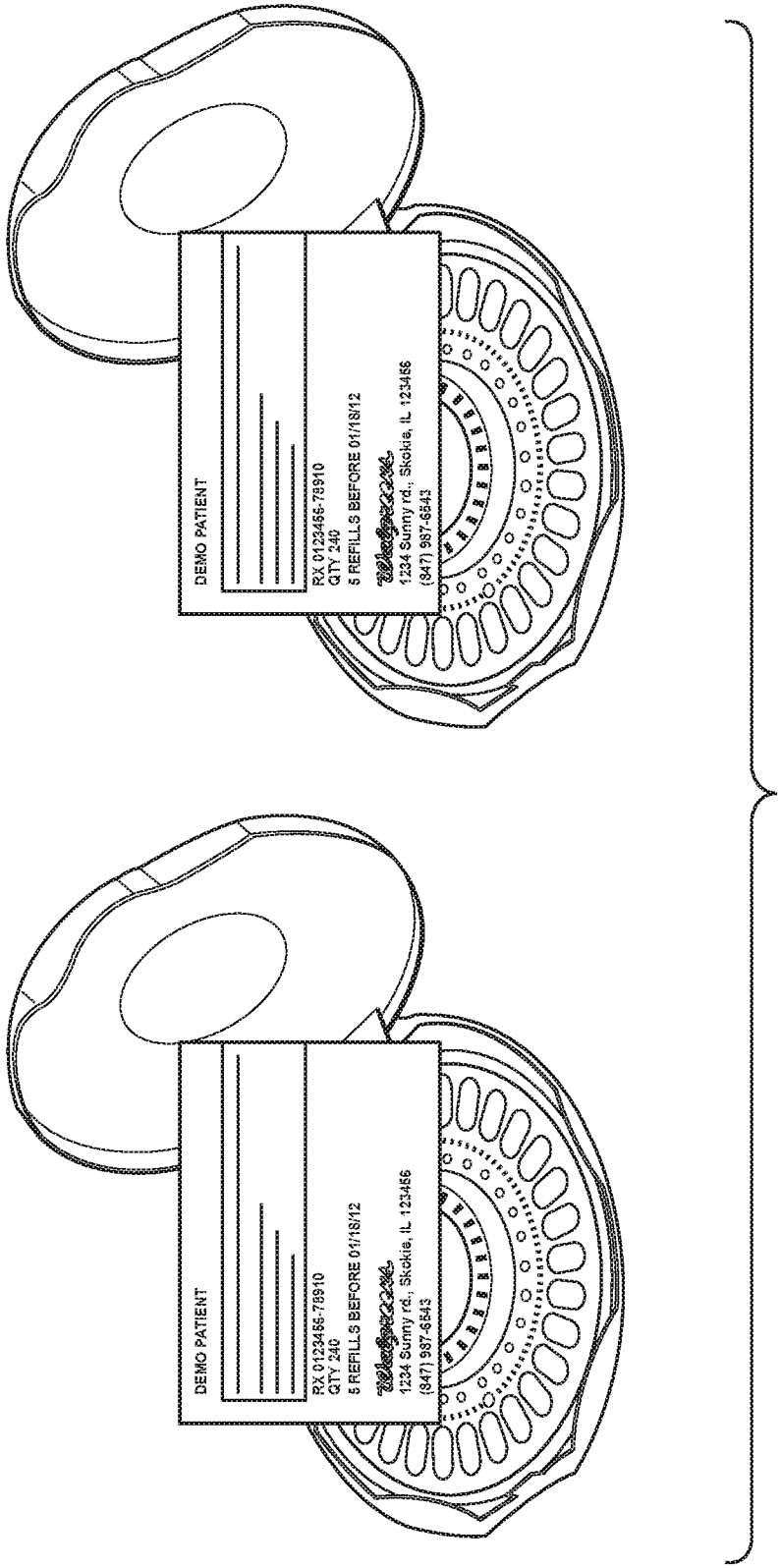
FIG. 24 illustrates images of a filled prescription, where the pharmaceutical product includes multiple units of birth control pills.

In an embodiment of the present disclosure involving dispensing multiple units of use (e.g., a two-month supply of birth-control pills as illustrated in FIG. 24), the technician may use the camera to take an image or images of as many of the unit that will fit into a single camera view. The technician should take care to make sure that the full product labels and product are visible in the images.

In an embodiment of the present disclosure involving dispensing controlled substances, substantially the same methods and processes as described above could be used.

While the systems and methods of the present disclosure are designed to minimize any filling process exceptions, the systems and methods of the present disclosure are capable of handling exceptions in the filling process. These exceptions may include, for example, a product not having a barcode, discrepancies in product weight, non-system drugs, and drug compounds. These exceptions may be handled by having the technician manually fill the prescription; place a filled vial, customer leaflet, prescription bag, and any other paperwork in a bin to be handed to the pharmacists; and have the pharmacist visually verify the filled prescription, for example.

In addition to the above-described embodiments of the present disclosure, a pharmacist may perform the steps of the method instead of a technician. In such cases, some of the steps of the method may be optional. For example, the image capture steps and the remote verification and approval steps may be bypassed.

The descriptions of various embodiments of the present disclosure have been provided for illustrative purposes. Revisions or modifications may be apparent to those of ordinary skill in the art without departing from this disclosure.

What is claimed is:

1. An image based and network controlled, security system configured to securely dispense pharmaceutical products onsite at a physical location, the image based and network controlled, security system comprising:

a pharmaceutical product imaging device positioned within a physically secured pharmacy area, the pharmaceutical product imaging device configured to capture a plurality of images of pharmaceutical products from multiple viewpoints;

a server communicatively coupled, through a computer network, to the pharmaceutical product imaging device, the server configured to store an account of a user; and a visualization user interface application configured to execute on a network computer positioned outside the physically secured pharmacy area, the network computer communicatively coupled, via a computer network, to the server, wherein the server is configured to:
receive, via the computer network, a scanned digital prescription image corresponding to a prescription of the user, determine, by a software program reading the scanned digital prescription image, a pharmaceutical product and a pharmaceutical product amount of the pharmaceutical product, receive, from the pharmaceutical product imaging device, digital images of the pharmaceutical product, the digital images captured from multiple viewpoints depicting features in the digital images such as shape, dimension, and/or markings of pharmaceutical product;

transmit, to the visualization user interface application executing on the network computer positioned outside the physically secured pharmacy area, a visual confirmation of the pharmaceutical product and the pharmaceutical product amount, the visual confirmation based on the one or more digital images of the pharmaceutical product, receive, from the visualization user interface application, a verification of the visual confirmation, and update, based on the verification, the user account with a ready state corresponding to the prescription, wherein the ready state indicates that the user may receive the pharmaceutical product.

2. The image based and network controlled, security system of claim 1, wherein the physically secured pharmacy area is at a first physical location, and wherein the network computer is at a second physical location, the first physical location remote to the second physical location.

3. The image based and network controlled, security system of claim 1 further comprising an automated counting device, the automated counting device configured to generate an automated confirmation of the pharmaceutical product amount, wherein the visual confirmation is based on upon the automated confirmation.

4. The image based and network controlled, security system of claim 3, wherein the automated counting device is a computer vision-based device.

5. The image based and network controlled, security system of claim 4, wherein computer vision-based device is configured to capture one or more digital images of a vial containing the pharmaceutical product and a prescription label affixed to the vial, the prescription label corresponding to the pharmaceutical product.

6. The image based and network controlled, security system of claim 5, wherein the one or more images of the prescription label are stored in a memory communicatively coupled to the server.

7. The image based and network controlled, security system of claim 6, wherein one or more images of each of the scanned digital prescription image, the prescription label, and the pharmaceutical product are transmitted to the network computer positioned outside the physically secured pharmacy area.

8. The image based and network controlled, security system of claim 7, wherein the server performs a visual comparison the one or more digital images of each of the scanned digital prescription image, the prescription label, and the pharmaceutical product, wherein the visual confirmation includes the visual comparison.

9. The image based and network controlled, security system of claim 7, wherein the network computer positioned outside the physically secured pharmacy area transmits to the server an indication of acceptance or denial of the pharmaceutical product, the ready state based on the indication.

10. The image based and network controlled, security system of claim 1, wherein the network computer is a mobile device.

11. An image based and network controlled, security method for securely dispensing pharmaceutical products onsite at a physical location, the image based and network controlled, image based and network controlled, security method comprising:

receiving, at a server via a computer network, a scanned digital prescription image corresponding to a prescription of a user, wherein the server is configured to store an account of a user;

determining, by a software program reading the scanned digital prescription image, a pharmaceutical product and a pharmaceutical product amount of the pharmaceutical product;

receiving, from a pharmaceutical product imaging device, digital images of the pharmaceutical product, wherein the digital images are captured from multiple viewpoints depicting features in the digital images such as shape, dimension, and/or markings of pharmaceutical product, and wherein the pharmaceutical product imaging device is positioned within a physically secured pharmacy area and is configured to capture a plurality of images of pharmaceutical products from multiple viewpoints;

transmitting, to a visualization user interface application executing on a network computer positioned outside the physically secured pharmacy area, a visual confirmation of the pharmaceutical product and the pharmaceutical product amount, the visual confirmation based on the one or more digital images of the pharmaceutical product;

receiving, from the visualization user interface application, a verification of the visual confirmation; and updating, based on the verification, the user account with a ready state corresponding to the prescription, wherein the ready state indicates that the user may receive the pharmaceutical product.

12. The image based and network controlled, security method of claim 11, wherein the physically secured pharmacy area is at a first physical location, and wherein the network computer is at a second physical location, the first physical location remote to the second physical location.

13. The image based and network controlled, security method of claim 11 further comprising generating, by an automated counting device an automated confirmation of the pharmaceutical product amount, wherein the visual confirmation is based on upon the automated confirmation.

14. The image based and network controlled, security method of claim 13, wherein the automated counting device is a computer vision-based device.

15. The image based and network controlled, security method of claim 14, wherein computer vision-based device is configured to capture one or more digital images of a vial containing the pharmaceutical product and a prescription label affixed to the vial, the prescription label corresponding to the pharmaceutical product.

16. The image based and network controlled, security method of claim 15, wherein the one or more digital images of the prescription label are stored in a memory communicatively coupled to the server.

17. The image based and network controlled, security method of claim 16, wherein one or more digital images of each of the scanned digital prescription image, the prescription label, and the pharmaceutical product are transmitted to the network computer positioned outside the physically secured pharmacy area.

18. The image based and network controlled, security method of claim 17, wherein the server performs a visual comparison the one or more digital images of each of the scanned digital prescription image, the prescription label, and the pharmaceutical product, wherein the visual confirmation includes the visual comparison.

19. The image based and network controlled, security method of claim 17, wherein the network computer positioned outside the physically secured pharmacy area transmits to the server an indication of acceptance or denial of the pharmaceutical product, the ready state based on the indication.

20. The image based and network controlled, security method of claim 11, wherein the network computer is a mobile device.

\* \* \* \* \*